US011696537B2

(12) United States Patent
Carvajal Alcaraz et al.

(10) Patent No.: US 11,696,537 B2
(45) Date of Patent: Jul. 11, 2023

(54) COMPOSITION AND METHOD FOR INCREASING THE CONTENT OF GLUCOSINOLATES IN ADULT PLANTS OF THE GENUS BRASSICA

(71) Applicants: CONSEJO SUPERIOR DE INVESTIGACIONES CIENTÍFICAS (CSIC), Madrid (ES); SAKATA SEED IBERICA, S.L.U., Valencia (ES)

(72) Inventors: Micaela Carvajal Alcaraz, Murcia (ES); Diego A. Moreno Fernandez, Murcia (ES); Juan Jose Rios Ruiz, Murcia (ES); Javier Bernabeu Durá, Valencia (ES); Agatha Agudelo Sanchez, Valencia (ES)

(73) Assignees: CONSEJO SUPERIOR DE INVESTIGACIONES CIENTIFICAS (CSIC), Madrid (ES); SAKATA SEED IBERICA, S.L.U., Valencia (ES)

(*) Notice: Subject to any disclaimer, the term of this patent is extended or adjusted under 35 U.S.C. 154(b) by 77 days.

(21) Appl. No.: 17/257,743

(22) PCT Filed: Jun. 28, 2019

(86) PCT No.: PCT/ES2019/070457
§ 371 (c)(1),
(2) Date: Jan. 4, 2021

(87) PCT Pub. No.: WO2020/008089
PCT Pub. Date: Jan. 9, 2020

(65) Prior Publication Data
US 2021/0282344 A1 Sep. 16, 2021

(30) Foreign Application Priority Data

Jul. 5, 2018 (ES) .............................. ES201830674

(51) Int. Cl.
*A01H 1/06* (2006.01)
*A01H 6/20* (2018.01)
*A01G 7/06* (2006.01)
*A01N 25/30* (2006.01)
*A01N 37/42* (2006.01)

(52) U.S. Cl.
CPC ................ *A01H 1/06* (2013.01); *A01G 7/06* (2013.01); *A01H 6/20* (2018.05); *A01N 25/30* (2013.01); *A01N 37/42* (2013.01)

(58) Field of Classification Search
CPC ... A01H 1/06; A01H 6/20; A01G 7/06; A01N 25/30; A01N 37/42
See application file for complete search history.

(56) References Cited

PUBLICATIONS

Tan et al, Journal of Asia-Pacific Entomology 14: 263-269 (Year: 2011).*

Tan et al. J. Asia-Pacific Entomology, 14: 263-269, 2011.*
Baenas et al. J. Agric. Food Chem, 62: 1881-1889, 2014.*
Michel et al. Water Air Soil Pollut. 227:66, pp. 1-11,2016.*
PHT; Break-Thru surfactant, retrieved from Google on Sep. 19, 2022.*
Anonymous, "Break-Thru S240 100% Polyether Modified Trisiloxane Super Spreader & Super Penetrant an Innovation". Brochure, Jul. 2015, pp. 1-4.
Santiago Perez-Balibrea, "Improving the Phytochemical Composition of Broccoli Sprouts by Elicitation", Journal, 2011, 35-44, vol. 129, Food Chemistry.
Moreno et al., "Basis for the new challenges of growing broccoli for health in hydroponics", SCI Journal of the Science of Food and Agriculture, 2008, vol. 88, Issue 8, pp. 1472-1481, 10 pages.
Dominguez-Perles et al., "Selecting cultivars of broccoli for optimal bioactive components: the influence of saline stress", International Society for Horticultural Science, AGRIS, 2014, Issue 939, 159-164, 6 pages.
Verkerk & Dekker, "Variation and Distribution of Glucosinolates in 42 Cultivars of Brassica Dleracea Vegetable Crops", ISHS Acta Horticulturae, vol. 856, International Symposium on Vegetable Safety and Human Health, 2010, 8 pages.
Dominguez-Perles et al., "Broccoli-derived by-products—a promising source of bioactive ingredients", The Society for Food Science & Technology, Institute of Food Technologists, Journal of Food Science, 2010, vol. 75, Issue 4, 10 pages.
Halkier & Gershenzon, "Biology and biochemistry of glucosinolates", Annu Rev Plant Biol., 2006, vol. 57, pp. 303-333, 34 pages.
Jeffery & Araya, "Physiological effects of broccoli consumption", SpringerLink, Phytochemistry Reviews, 2009, vol. 8, pp. 283-298, 16 pages.
Keen, "Specific elicitors of plant phytoalexin production: detenninants of race specificity in pathogens?", Science AAAS, 1975, vol. 187, Issue 4171, pp. 74-75, 2 pages.
Ku et al., "Transcriptome and Metabolome Analyses of Glucosinolates in Two Broccoli Cultivars Following Jasmonate Treatment for the Induction of Glucosinolate Defense to Trichoplusia ni (Hübner)", International Journal of Molecular Science, 2016, vol. 17, Issue 7, 17 pages.
Baenas et al., "Elicitation: A Tool for Enriching the Bioactive Composition of Foods", Molecules, 2014, vol. 19, Issue 9, pp. 13541-13563, 23 pages.
Conrath et al., "Priming for Enhanced Defense", Annual Review of Phytopathology, 2015, vol. 53, pp. 97-119, 26 pages.

(Continued)

*Primary Examiner* — Keith O. Robinson
(74) *Attorney, Agent, or Firm* — Hayes Soloway PC (57) ABSTRACT

The present invention relates to a composition comprising methyl jasmonate and a polysiloxane polyether for increasing the content of glucosinolates in adult plants of the genus *Brassica*, for example, broccoli. By means of foliar application of the composition on adult plants having a developed cuticle, a significant increase is achieved in the concentrations of glucosinolates (mainly glucoraphanin and neoglucobrassicin), in the floret of the plants, without degrading the organoleptic properties thereof.

16 Claims, 3 Drawing Sheets

(56) References Cited

PUBLICATIONS

Villarreal-Garcia et al., "Plants as Biofactories: Postharvest Stress-Induced Accumulation of Phenolic Compounds and Glucosinolates in Broccoli Subjected to Wounding Stress and Exogenous Phytohormones", Frontiers in Plant Science, 2016, vol. 7, Article 45, 11 pages.

Baenas et al., "Biotic Elicitors Effectively Increase the Glucosinolates Content in Brassicaceae Sprouts", Journal of Agricultural and Food Chemistry, 2014, vol. 62, Issue 8, pp. 1881-1889, 9 pages.

Yi et al., "Exogenous Methyl Jasmonate and Salicylic Acid Induce Subspecies-Specific Patterns of Glucosinolate Accumulation and Gene Expression in Brassica oleracea L.", Molecucles, 2016, vol. 21, 22 pages.

Kim & Juvik, "Effect of Selenium Fertilization and Methyl Jasmonate Treatment on Glucosinolate Accumulation in Broccoli Florets", Journal of the American Society for Horticultural Science, 2011, vol. 136, Issue 4, pp. 239-246, 8 pages.

Ku et al., "Optimization of methyl jasmonate application to broccoli florets to enhance health-promoting phytochemical content". Society of Chemistry Industry, Journal of the Science of Food and Agriculture, 2014, vol. 94, pp. 2090-2096, 7 pages.

Dominguez-Perles et al., "Broccoli-derived by-products-a promising source of bioactive ingredients", The Society for Food Science & Technology, Journal of Food Science, 2010, vol. 75, Issue 4, 10 pages.

Martinez-Sanchez et al., "Microbial, nutritional and sensory quality of rocket leaves as affected by different sanitizers", ScienceDirect, Elsevier, 2006, vol. 42, pp. 86-97, 12 pages.

Baenas et al., "Selecting Sprouts of Brassicaceae for Optimum Phytochemical Composition", American Chemical Society, Journal of Agricultural and Food Chemistry, 2012, vol. 60, Issue 45, pp. 11409-11420, 12 pages.

Sripontan & Hwang, "Jasmonate-induced defense in tomato and cabbage deterred Spodoptera litura (Noctuidae) growth", Elsevier, Journal of Asia-Pacific Entomology, 2016, vol. 19, pp. 1125-1129, 5 pages.

Tan et al., "Methyl jasmonate induced responses in four plant species and its effect on Spodoptera litura Fab. performance", Journal of Asia-Pacific Entomology, 2011, vol. 14, pp. 263-269, 7 pages.

Liu et al., "Enhancement of Broccoli Indole Glucosinolates by Methyl Jasmonate Treatment and Effects on Prostate Carcinogenesis", Journal of Medicinal Food, 2014, vol. 17, Issue 11, pp. 1177-1182, 6 pages.

Ku et al., "Optimization of methyl jasmonate application to broccoli florets to enhance health-promoting phytochemical content". Journal of the Science of Food and Agriculture, 2014, vol. 94, pp. 2090-2096, 7 pages.

* cited by examiner

COMPOSITION AND METHOD FOR INCREASING THE CONTENT OF GLUCOSINOLATES IN ADULT PLANTS OF THE GENUS BRASSICA

CROSS-REFERENCE TO RELATED APPLICATIONS AND PRIORITY

This patent application claims priority from PCT Patent Application No. PCT/ES2019/070457 filed Jun. 28, 2019, which claims priority from Spanish Patent Application No. P201830674 filed Jul. 5, 2018. Each of these patent applications are herein incorporated by reference in their entirety.

The present invention relates to a composition and a method for increasing the content of glucosinolates in adult plants of the genus *Brassica*, preferably those used in human food, such as broccoli, by means of foliar application once the vegetative reproductive phase of the plant has been reached, without any degradation of the organoleptic properties of the parts of the plant intended for human food.

BACKGROUND OF THE INVENTION

Broccoli, a plant of the order Brassicales, is a rich source of bioactive compounds among which include, in particular, glucosinolates, compounds of secondary metabolism with nitrogen and sulphur in the molecule thereof, which are currently the focus of much scientific attention given their implications in plant physiology (plant defence) and in food quality and bioactivity (organoleptic quality and functionality). These compounds are almost exclusively found in cruciferous vegetables (order Capparales) and are hydrolysed when they come in contact with the enzyme myrosinase (plant glucosidase) and by the action of glucosidases of the gut microbiota, giving rise to isothiocyanates, bioactive compounds, which are involved in the detoxifying mechanisms of cells through different stimulation and inhibition mechanisms of certain enzymes. Two of the glucosinolates that can be found in broccoli cultivars (*Brassica oleracea* var. *Italica*) are glucoraphanin and neoglucobrassicin. The hydrolysed derivatives of these glucosinolates give rise to isothiocyanate sulforaphane (from glucoraphanin) and indole-3-carbinol (from glucobrassicin and related compounds thereof). Both have drawn the attention of very different research groups worldwide due to their implication in protective, antioxidant and antitumour properties against free radicals resulting from the consumption of broccoli (Moreno, D. A. et al. (2008) *Journal of the Science of Food and Agriculture* 88, 1472-1481). Therefore, broccoli, either fresh or as a derived ingredient, offers the possibility of developing foods fortified with bioactive compounds that help reduce the incidence of diseases, with the consequent importance in the agri-food industry (Dominguez-Perles, R. et al. (2012) *Acta Horticulturae*, 939, 159-163). In fact, it is recognised as "the vegetable with the highest nutritional value" in relation to the weight of the edible part.

Figure 1:
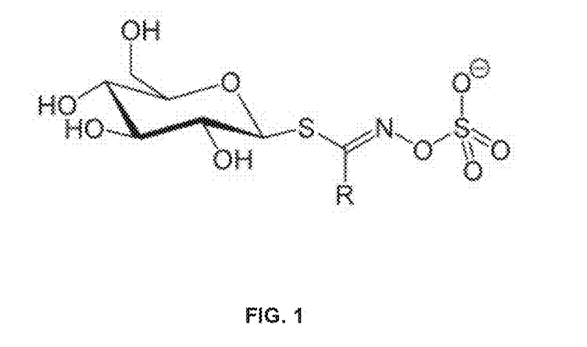
FIG. 1 shows the basic structure of a glucosinolate.

The aforementioned glucosinolates, also called "thioglucosides", are nitrogen-sulphur, anionic secondary metabolites exclusively found in the family Brassicaceae (Verkerk, R. et al. (2010) *Acta Horticulturae* vol. 856, p. 63-69). The basic skeleton of glucosinolates (β-D-thioglucoside-N-hydroxysulphate) consists of a β-D-thioglucose group, a sulfonated oxime and a side chain derived from methionine, phenylalanine, or tryptophan amino acids (FIG. 1). The chemical structure of glucosinolates can vary between species and between varieties within the same species (Dominguez-Perles, R. et al. (2010) *Journal of Food Chemistry* 75, 383-392). According to the side chain, glucosinolates can be broadly classified as: aliphatic, aromatic, benzoic, multiple glycosylated, with sulphur in the side chain thereof and heterocyclic or indolic (Halkier, B. A. et al. (2006). *Annual Review of Plant Biology*, 57(1), 303-333). In the case of broccoli, the most representative glucosinolates are aliphatic, aromatic and indolic (A).

| STRUCTURE | GLUCOSINOLATE |
|---|---|
| Aliphatic | Glucoiberin (GI) |
| | Glucoraphanin (GR) |
| | Glucoerucine (GE) |
| Aromatic | Gluconasturtine (GN) |
| Indolic | Glucobrassicin (GB) |
| | Neoglucobrassicin (NGB) |

Glucosinolates have several important physiological properties and constitute a defence mechanism for the plant against herbivores and pathogens, which at high concentrations produce metabolic stress in invertebrate herbivores, thus affecting the growth thereof.

They have biological properties of interest for preventing some diseases in humans that consume them (Jeffery, E. H. et al. (2009). *Phytochemistry Reviews*, vol. 8, 283-298). Moreover, they contribute to maintaining body tissues, increasing resistance to infection, regulating the correct development of the nervous system and intervening in growth, and they are beneficial for producing enzymes in the liver (Moreno, D. A. et al. (2008). *Journal of the Science of Food and Agriculture*. 88, 1472-1481; Jeffery, E. H. et al. (2009). *Phytochemistry Reviews*, vol. 8, 283-298).

Elicitors or biostimulators are natural substances that induce physiological changes in the plant, activating the defence mechanisms thereof. Plants respond to these factors by activating a number of mechanisms, similar to defence responses to infection by pathogens or environmental stimuli, which affect plant metabolism and improve the synthesis of phytochemicals or secondary metabolites. The first biotic elicitors were described in the early 1970s (Keen, N. T. (1975) *Science* 187, 74-75). Since then, numerous publications have accumulated evidence of the application of compounds that induce defence responses in intact plants such as broccoli (Ku K M et al. (2016) *Int J Mol Sci.* 15, 17(7), 1135). Elicitors are also used as a tool to improve the phytochemical content in plants for the purposes of improving food, applied alone or in combination at selected points in time of the plant growth (for a review see: Baenas, N. et al. (2014). *Molecules,* 19(9), 13541-13563). Elicitors can be classified as biotic and abiotic compounds, and plant hormones (salicylic acid, jasmonates, etc.) can also be considered elicitors.

Elicitation can be used as a pre-harvest or post-harvest treatment. Among the pre-harvest treatments, seed preparation ("priming") is also considered, which consists of hydrating the seeds in a solution with the elicitor in order to induce the defence response of cells. Thus, for example, it has been observed that parsley seeds treated with jasmonate showed an increase in antioxidant systems and the induction of defence systems through the synthesis of phenylpropanoids (Conrath, U. et al. (2015) *Annual Review of Phytopathology* 53, 97-119). Elicitors can also be applied as a gas in a closed environment (such as MeJA), in liquid form to a hydroponic solution or by exogenous aerosols.

Jasmonic acid (JA) and the methyl ester thereof, methyl jasmonate (MeJA), are widely known to generate a broad range of compounds by inducing the expression of plant genes for various biosynthetic pathways. These small signalling molecules also defined as "hormones" are induced in cells in response to injury or attack by pathogens in plants and they can, in turn, induce cellular responses at low concentrations distant from the synthesis site thereof.

In post-harvest practices, treatments with specific elicitors have been used to improve the phytochemical content and quality of foods such as broccoli (Villarreal-Garcia D. et al (2016) *Front Plant Sci.* 10; 7:45). The results concluded that a simple and effective treatment with MeJA improved the content of individual glucosinolates and phenolic components in broccoli during storage, protecting it from contamination in wounds.

Research in recent years has demonstrated the potential of applying JA and MeJA in Brassicas to increase the concentration of bioactive compounds such as glucosinolates. Almost all of the articles focus on applications and determinations in sprouts (Baenas, N. et al. (2014) *Journal of Agricultural and Food Chemistry*, 62, 1881-1889) and in leaves of young plants (Yi, G E et al. (2016) *Molecules* 24, 21(10)), i.e., in plants without a developed cuticle, although there is some research with applications in inflorescence (Kim, H. S. et al. (2001) *J. Amer. Soc. Hort. Sci.* 136(4): 239-246).

In addition, surfactants are substances that have an effect through the surface tension on the contact surface between two phases and that can, for example, facilitate the penetration of molecules (biocides, fertilisers, elicitors, etc.) in plants. The number of surfactants known in the state of the art is very high and the activity and effect thereof depend on many factors, such as the plant species, the physiological state thereof (presence of cuticle or not) or environmental conditions. It can even cause negative effects on the colouring or shape of the edible parts of the plant, including the edible part of broccoli (*Brassica oleracea* ssp. *Italica*) when combined with methyl jasmonate (*J Sci Food Agric* 2014; 94: 2090-2096), an aspect which implies considerable negative depreciation or decrease in production for the producer.

The object of the present invention is a composition that is based on the combination of an elicitor such as methyl jasmonate and a surfactant such as polysiloxane polyether, which can be used by means of foliar application on adult plants of the genus *Brassica* having a developed cuticle, preferably those used in human food and more preferably broccoli, achieving a significant increase in the concentrations of glucosinolates (mainly glucoraphanin and neoglucobrassicin) in the florets, without degrading the organoleptic properties thereof. Moreover, the application thereof enables a secondary metabolite to appear which is identified for the first time in plants of the order Brassicales, specifically a feruloyl-indol-glucosinolate (hereinafter, feruloyl-GLS).

DESCRIPTION OF THE INVENTION

In a first aspect, the present invention relates to a composition characterised in that it comprises methyl jasmonate (MeJA), a polysiloxane polyether, water and a C2-C4 alcohol, preferably ethanol.

In a preferred embodiment, the C2-C4 alcohol is ethanol.

In a more preferred embodiment, the composition of the invention consists of methyl jasmonate (MeJA), a polysiloxane polyether, water and a C2-C4 alcohol, preferably ethanol.

Polysiloxane polyether is a polyether-modified polysiloxane copolymer, preferably with surfactant activity. In the present invention, polysiloxane polyether will also be called modified polysiloxane polyether (MPP).

Polysiloxane polyethers suitable for use thereof in the present invention are known in the state of the art and are commercially available. For example, modified polysiloxane polyethers are available under the Break-Thru 9902™, Break-Thru 9903™, Break-Thru 5503™, Break-Thru 9907™ and Break-Thru 9908™ brand.

More preferably, polysiloxane polyether is a non-ionic trisiloxane, for example, the one available under the BREAK-THRU® S 233 brand.

The concentration of methyl jasmonate in the final composition is between 50 and 500 μmolar; more preferably, the concentration of methyl jasmonate in the composition is 100 μmolar.

In a preferred embodiment of the invention, the composition comprises
methyl jasmonate between 0.0015% and 0.0028% by volume,
polysiloxane polyether between 0.068% and 0.1272% by volume,
C2-C4 alcohol between 0.15 and 0.28% by volume, and
water up to 100% of the volume (i.e., water between 99.7805 and 99.59% by volume).

A more preferred embodiment of the composition of the invention consists of: 0.0022% by volume of MeJA, 0.2% by volume of ethanol, 0.1% by volume of polysiloxane polyether and water to a total volume of 100%.

The use of MeJA as an elicitor in combination with a polysiloxane polyether leads to a significant increase in the concentrations of glucosinolates and the generation of a feruloyl-GLS metabolite in the plants to which it is applied, even when using minimal amounts of the MeJA elicitor.

Another aspect of the invention relates to a method for increasing the content of glucosinolates in adult plants of the genus *Brassica* comprising the following steps:

a) carrying out a first foliar application of the composition defined in the first aspect of the invention at the time the flower bud appears on the plant;
b) carrying out a second foliar application of the composition defined in the first aspect of the invention five days after the first application;
c) carrying out a third foliar application of the composition defined in the first aspect of the invention five days after the second application.

This method increases the content of glucosinolates both on the inflorescence and on the leaves without producing any decrease in the organoleptic or commercial properties, preferably, production, colour, compaction, shape and taste of the first.

In the present invention, glucosinolates are preferably selected from glucoraphanin, glucobrassicin, methoxyglucobrassicin, neoglucobrassicin and combinations thereof, more preferably, neoglucobrassicin.

Furthermore, and surprisingly, at least one compound (secondary metabolite) is also obtained through this method, preferably a feruloyl-indole-glucosinolate, in which a phenolic acid and an indolic glucosinolate are joined together (tentatively, neoglucobrassicin, NGB).

As far as is known, this is the first time that this secondary metabolite in plants of the order Brassicales is described, derived from glucosinolate and phenolic compound, which can be a compound for mobilising glucosinolates between organs of the plant. Furthermore, and given that the components of the secondary metabolite each have beneficial effects on the health of the person who ingests them, it is expected that the combination of both will also preserve this effect.

The magnitude of the increase in the concentration of glucosinolates obtained with the application of the composition of the invention, using a very low concentration of the MeJA elicitor (preferably not greater than 100 μmolar), requires concentrations in other tests performed with the same elicitor and collected in the state of the art that are much higher in order to reach the same magnitude (see examples of the present invention).

In a preferred embodiment of the invention, the plant of the genus *Brassica* is selected from the list comprising broccoli, cauliflower, cabbage, rapini, Brussels sprouts, swede, turnip, kohlrabi, kale and rapeseed. Even more preferably, the plant is broccoli.

In a preferred embodiment of the invention, an amount between 100 and 150 ml of the composition is applied in each of the foliar applications per plant.

Preferably, the foliar application of the composition is by spray.

In a more preferred embodiment of the method of the invention:
- the foliar application of the composition is by spray, applying an amount between 100 and 150 ml of the composition per broccoli plant in each application.
- the composition comprises 0.0022% by volume of MeJA, 0.2% by volume of ethanol, 0.1% by volume of polysiloxane polyether and water to a total volume of 100%.

The method of the invention enables functional foods to be obtained which, in addition to the usual nutritional effects thereof, have biological compounds with an added positive selective effect on one or more functions of the organism and which have beneficial effects on health, improving it or reducing the risk of disease. All this is due to the fact that the synthesis and content of glucosinolates and of at least one secondary metabolite derived from glucosinolate and phenolic compound (feruloyl-GLS) in the different tissues of plants, including the florets thereof, increase significantly, using very low concentrations of methyl jasmonate when the plants have developed the cuticle thereof, without damaging them.

A final aspect of the present invention relates to the use of the composition to improve defence mechanisms against herbivores and pathogens in a plant of the order Brassicales.

Until now, in the state of the art, the possibility of increasing the glucosinolates of plants of the genus *Brassica*, such as broccoli by means of methyl jasmonate, alone or combined with a surfactant, both on sprouts and on leaves and inflorescence, has been described. In the present invention, methyl jasmonate in combination with a polysiloxane polyether is applied in a lower concentration on leaves and it achieves an increase in the glucosinolates on leaves and on florets, as well as the generation of at least one secondary metabolite derived from glucosinolate and phenolic compound, a feruloyl-GLS, with only three applications. This increase is observed, moreover, in different broccoli cultivars. Furthermore, the composition of the invention does not lead to a reduction in the organoleptic properties as described in the publications included in the state of the art and this is demonstrated in the results in Table 4 of the present invention, using a combination of methyl jasmonate and a surfactant of a different nature.

In the present invention, the term "adult plant" refers to a plant that has completed the vegetative period thereof and passes to the reproductive period. Adult plants have a thicker cuticle than those found in the initial stages of the vegetative period. In fact, in the reproductive phase of plant development, the cuticle of the leaf reaches the maximum thickness thereof. The cuticle is a layer of lipid polymers impregnated with waxes that is present on the external surfaces of the primary organs of all vascular land plants. The cuticle forms a homogeneous outer covering, the function of which is to prevent water permeability to prevent evaporation from the cells of the epidermis.

The term "flower bud" refers to the inflorescence primordium that emerges from the apical bud of the main stem. Stage in which the inflorescence covered by small leaves for protecting it begins to develop.

The term "floret" or "head" refers to the immature or developing inflorescence. It is the main organ for food consumption in the shape of a compound corymb, developed from the flower bud. It is made up of numerous flower primordia supported on flower stems or pedicels, which in turn are arranged on succulent peduncles.

The term "organoleptic properties" refers to properties that are measured through the senses. This sensory analysis is based on the basic parameters of colour, shape, size, smell, texture, taste and temperature. In the present invention, they preferably refer to colour, compaction, roundness and taste.

The term "C2-04 alcohol" refers to an organic alcohol with a carbon number ranging from two to four. For example: ethanol, propanol, butanol, tert-butanol, isobutanol.

Throughout the description and the claims, the word "comprises" and its variants do not intend to exclude other technical features, additives, components or steps. For those skilled in the art, other objects, advantages and features of the invention may be partially deduced from both the description and the embodiment of the invention. The following examples and figures are provided by way of illustration, and are not intended to limit the present invention.

EXAMPLES

The invention will be illustrated below by means of several tests carried out by the inventors which demonstrate the effectiveness of the composition and method of the invention.

Material and Methods

Field Test

Seedlings of three broccoli cultivars (*Brassica oleracea* var. *Italica*) obtained from a seedbed where the seeds grew for 30 days were used. Specifically, the cultivars were Ares, Parthenon and Marathon, all of them from the SAKATA company. The experiment was carried out during the autumn/winter period at an experimental farm in the Mirador field in the municipality of San Javier (Murcia) and under a semi-arid Mediterranean climate. The average daily temperature and relative humidity were calculated from measurements taken every 10 minutes using a data logger. The humidity reached in the plot was 50/80% (day/night) and the air temperature ranged between 24/8° C. during the day and night, respectively.

A total of 40 plants to be cultivated were planted, 20 for each treatment. All the seedlings were planted on the same day, under the same conditions and irrigated with fertigation [2 dS $m^{-1}$ electrical conductivity (EC)] twice a day for 10 minutes for the first 45 days, and then for 15 minutes for the next 45 days.

Once they reached the reproductive phase, which is when the flower bud appears (approximately 120 days after sowing the seeds in the seedbed), the treatments were applied using Composition 1 and the Control Composition and performed three times on the leaf. One at the time the flower bud appears and the following applications 5 and 10 days, respectively, after the first application. Each application was carried out by spray, applying 100-150 ml per plant. The leaves and inflorescences were collected for analysis once they reached the commercial size thereof (approximately 18 days after the appearance of the flower bud) and they were frozen in liquid nitrogen and immediately lyophilised to prevent the compounds of interest from degrading until it was time to determine the glucosinolates and other metabolites.

While the treatments were applied, irrigation by fertigation was maintained under the same conditions under which it was carried out before applying the treatments.

Composition 1: A solution was prepared containing 0.0022% by volume of MeJA (for a final concentration of 100 micromolar in the composition), 0.2% by volume of ethanol, 0.1% by volume of polysiloxane polyether (Break-Thru S 233 ®) and 99.6978% by volume of water.

Control Composition: The control treatment consisted of applying a solution containing 0.1% by volume of polysiloxane polyether and 99.9% by volume of water.

Greenhouse Test

In a growth chamber, seeds of the broccoli cultivar (Brassica oleracea var. Italica) Parthenon which grew for 30 days were germinated. Subsequently, they were allowed to grow in a greenhouse for 75 days until the inflorescences reached commercial size. In this case, foliar application of the treatments indicated below was carried out by spraying between 100 and 150 ml per plant: one at the time the flower bud appears and the following applications 5 and 10 days, respectively, after the first application.

Control composition: consisting of a solution containing 0.2% by volume of ethanol and 99.8% by volume of water.

Surfactant composition 1 (Triton X-100): consisting of a solution containing 0.1% by volume of Triton X-100 surfactant and 99.9% by volume of water.

Surfactant composition 2 (MPP): consisting of a solution containing 0.1% by volume of the modified polysiloxane polyether surfactant and 99.9% by volume of water.

Elicitor composition (MeJA): consisting of a solution containing 0.0022% by volume of MeJA, 0.2% by volume of ethanol and 99.7978% by volume of water.

Composition 2 (MeJA+Triton X-100): consisting of a solution containing 0.0022% by volume of MeJA, 0.2% by volume of ethanol, 0.1% by volume of Triton X-100 and 99.70% by volume of water.

Composition 1 (MeJA+MPP): A solution was prepared containing 0.0022% by volume of MeJA (for a final concentration of 100 micromolar in the composition), 0.2% by volume of ethanol, 0.1% by volume of polysiloxane polyether and 99.7968% by volume of water.

Subsequently, the plants were harvested and the leaves and inflorescences were frozen in liquid nitrogen and immediately lyophilised to prevent the compounds of interest from degrading until it was time to determine the glucosinolates and metabolites of interest.

Determining Glucosinolates and a Feruloyl-GLS

The analyses were carried out on the leaf and inflorescence at the time of collecting the commercial size. The method used for extracting glucosinolates was based on the method developed by the research group and currently in the public domain: Dominguez-Perles et al. (2010) *Journal of Food Science* 75, 383-392. The quantitative analysis was carried out by HPLC-DAD. The lyophilised and ground samples (100 mg) were extracted with 1 ml of 70% MeOH in a hot bath at 70° C. for 30 minutes, stirring every 5 minutes in a vortex, to optimise the extraction. The reaction was then stopped in an ice bath and the samples were centrifuged to precipitate the insoluble material, for 15 minutes, at 10,000 g and at 4° C. The supernatant was collected and the methanol was removed on a rotary evaporator with a thermostatically controlled bath at 38° C. The dry residue obtained was redissolved in ultra-pure water and filtered (00.22 μm of PVDF) for the subsequent analysis thereof.

Each sample (20 μl) was analysed in high-performance liquid chromatography (HPLC) equipped with a pump for binary eluent partitioning, an inline degasser, a photodiode detector autosampler (DAD). The compounds were separated in a C18 column measuring 250×4 mm and with a 0.4 um pore diameter, in reversed phase liquid chromatography (RP-HPLC) mode. The glucosinolates were identified using the methodology already described by the research group and publicly available for multipurpose analysis of intact glucosinolates (Martinez-Sánchez et al. 2006 *Postharvest Biol. Technol.* 42, 86-97; Dominguez-Perles et al. (2010) *Journal of Food Sci.* 75, 383-392), based on the retention times of the respective analytical peaks, the maximum absorption spectra thereof in the UV-Vis range and the comparison with commercially available external standards, sinigrin for aliphatic glucosinolates and glucobrassicin for indolic glucosinolates (Baenas et al. (2012) *J. Agric. Food Chemistry*, 60, 11409-11420). The detection was carried out at 227 nm and the concentration of glucosinolates was expressed in μmol/g of plant tissue dry weight.

Figure 2:
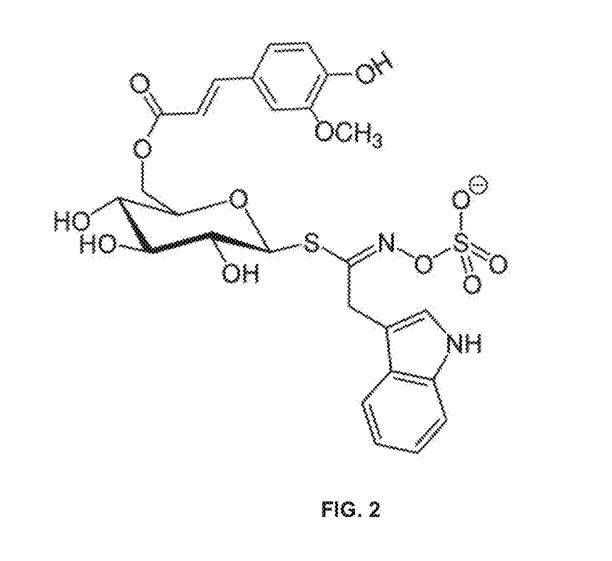
FIG. 2 shows the chemical structure of a feruloyl-indole-glucosinolate, wherein the indolic glucosinolate is neoglucobrassicin.
Figure 4:
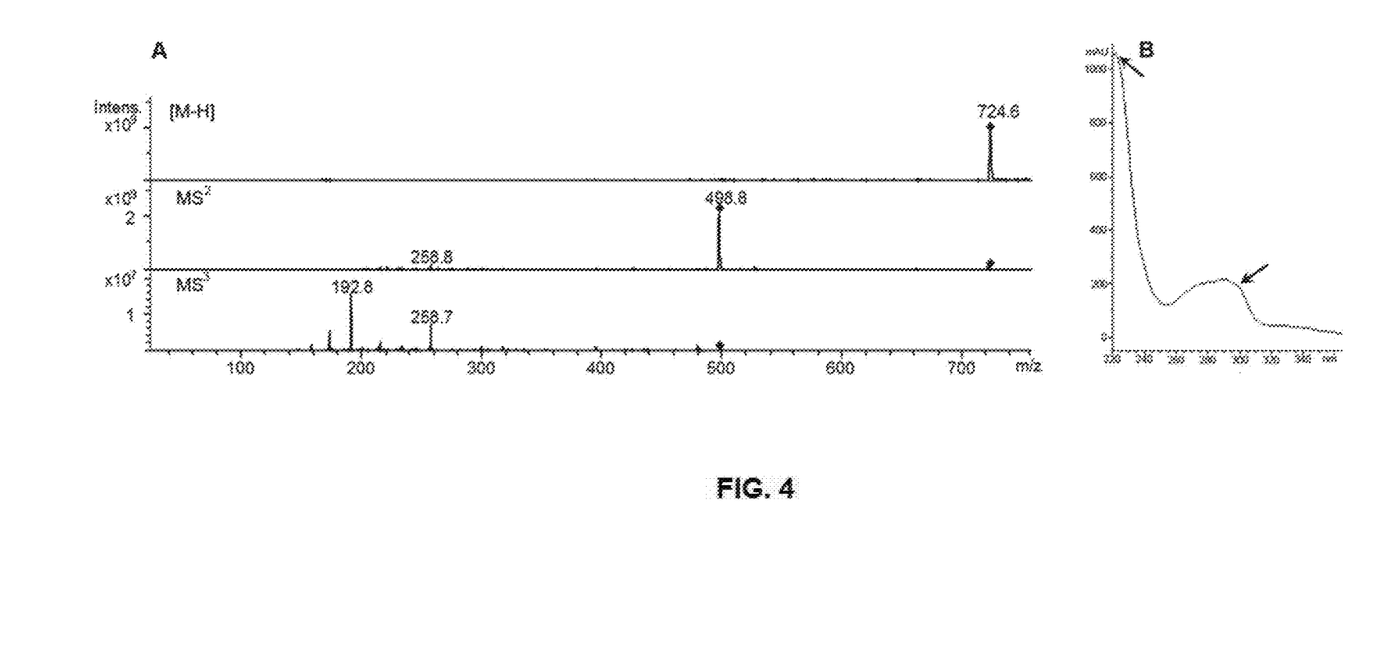
FIG. 4 shows an absorption spectrum (UV-Vis) with maximum absorption peaks coinciding with a feruloyl-GLS, the arrows indicating the maximum absorption peaks at 227±3 nm (GLS) and 320±16 nm (hydroxycinnamic acids such as ferulic acid).

The spectrum type of feruloyl-GLS (see FIGS. 2 and 4) in which a phenolic acid and an indolic glucosinolate are joined together (tentatively, neoglucobrassicin, NGB) was determined by HPLC-DAD-ESI-MS/MS fragmentation, observing the parental ion of 724 (M-H, m/z, 100%) and the resulting fragments of 499 m/z (100%), 259 m/z (10.2%, glucosinolate indicator) and 193 m/z (100%, derived feruloyl indicator).

The results of applying the treatments in the two tests carried out are shown below.

Field Test

Table 1. Concentration of glucosinolates and a feruloyl-GLS on leaves of different cultivars of *Brassica oleracea* var. *Italica* recorded in the field test using different treatments.

TABLE 1

| Variety | Treatment | mg GRA/g DW | mg GBS/g DW | mg MGB/g DW | mg NGB/g DW | mg F-GLS/g DW | Total GLSs |
|---|---|---|---|---|---|---|---|
| Ares | Control | 0.59 ± 0.03 | 0.42 ± 0.07 | 0.55 ± 0.07 | 1.38 ± 0.11 | tr | 2.94 ± 0.15 |
| Ares | Composition | 0.63 ± 0.04 | 0.56 ± 0.05 | 0.69 ± 0.05 | 1.43 ± 0.09 | 0.01 ± 0.001 | 3.31 ± 0.16 |
| Parthenon | Control | 1.03 ± 0.10 | 1.09 ± 0.11 | 0.30 ± 0.05 | 1.17 ± 0.10 | tr | 3.59 ± 0.11 |
| Parthenon | Composition 1 | 1.11 ± 0.10 | 2.25 ± 0.15 | 0.33 ± 0.04 | 2.04 ± 0.18 | 0.01 ± 0.001 | 5.73 ± 0.43 |
| Marathon | Control | 0.60 ± 0.10 | 1.09 ± 0.23 | 0.24 ± 0.04 | 0.28 ± 0.05 | tr | 2.21 ± 0.28 |
| Marathon | Composition 1 | 0.77 ± 0.05 | 2.61 ± 0.14 | 0.41 ± 0.02 | 1.53 ± 0.11 | 0.01 ± 0.002 | 5.32 ± 0.24 |

GR: Glucoraphanin
GB: Glucobrassicin
MGB: Methoxyglucobrassicin
NGB: Neoglucobrassicin
F-GLS: Feruloyl-glucosinolate
Tr: concentration in trace amounts
DW. Dry weight Table 2. Concentration of glucosinolates and a feruloyl-GLS in inflorescences of different cultivars of *Brassica oleracea* var. *Italica* recorded in the field test using different treatments.

TABLE 2

| Variety | Treatment | mg GRA/g DW | mg GBS/g DW | mg MGB/g DW | mg MGB/g DW | mg F-GLS/g DW | Total GLSs |
|---|---|---|---|---|---|---|---|
| Ares | Control | 1.15 ± 0.04 | 1.05 ± 0.05 | 0.48 ± 0.03 | 1.65 ± 0.08 | tr | 4.33 ± 0.13 |
| Ares | Composition 1 | 1.61 ± 0.26 | 0.77 ± 0.11 | 0.58 ± 0.05 | 2.51 ± 0.1 | 0.03 ± 0.01 | 5.50 ± 0.19 |
| Parthenon | Control | 1.75 ± 0.04 | 2.12 ± 0.16 | 0.50 ± 0.05 | 1.10 ± 0.25 | tr | 5.48 ± 0.21 |
| Parthenon | Composition 1 | 2.02 ± 0.11 | 2.01 ± 0.14 | 0.70 ± 0.02 | 4.48 ± 0.06 | 0.25 ± 0.02 | 9.47 ± 0.42 |
| Marathon | Control | 1.74 ± 0.10 | 1.77 ± 0.07 | 0.41 ± 0.02 | 1.14 ± 0.05 | tr | 5.06 ± 0.53 |
| Marathon | Composition 1 | 2.01 ± 0.16 | 2.11 ± 0.20 | 0.62 ± 0.03 | 4.65 ± 0.18 | 0.28 ± 0.03 | 8.68 ± 0.15 |

GR: Glucoraphanin
GB: Glucobrassicin
MGB: Methoxyglucobrassicin
NGB: Neoglucobrassicin
F-GLS: Feruloyl-glucosinolate
Tr: concentration in trace amounts
DW. Dry weight Tables 1 and 2 show that the foliar application of the composition of the invention (Composition 1) in adult plants that have reached the reproduction phase and have a developed cuticle causes, for plants of crops different from the Ares, Parthenon and Marathon cultivars, an obvious effect on the increase in the concentration of individual glucosinolates (GRA: Glucoraphanin, MGB: Methoxyglucobrassicin and NGB: Neoglucobrassicin), both on leaf and on inflorescence, and the appearance of a feruloyl-GLS, also on inflorescences and on elicited leaves.

Furthermore, no decrease in the organoleptic properties of the inflorescences obtained in this test were recorded.

Greenhouse Test

Table 3. Concentration of glucosinolates on leaves and inflorescences of the Parthenon cultivar in the greenhouse test using different treatments

| LEAF (mg/g DW) Parthenon | mg GRA/g DW | mg GBS/g DW | mg NGB/g DW | feruloyl-GLS/g DW | Total GLS |
|---|---|---|---|---|---|
| Control | 0.37 ± 0.02 | 0.73 ± 0.12 | 0.71 ± 0.12 | — | 1.81 ± 0.05 |
| Triton X-100 | 0.35 ± 0.06 | 0.70 ± 0.14 | 0.69 ± 0.15 | — | 1.74 ± 0.05 |
| MPP | 0.33 ± 0.04 | 0.68 ± 0.12 | 0.68 ± 0.12 | — | 1.69 ± 0.05 |
| MeJA | 0.35 ± 0.06 | 0.71 ± 0.12 | 0.69 ± 0.14 | — | 1.75 ± 0.05 |
| MeJA + Triton X-100 | 0.29 ± 0.08 | 1.34 ± 0.11 | 3.41 ± 0.25 | — | 5.05 ± 0.06 |
| MeJA + MPP | 0.58 ± 0.21 | 1.36 ± 0.3 | 5.62 ± 0.38 | 1.68 ± 0.01 | 9.23 ± 0.18 |

| INFLORESCENCE (mg/g DW) Parthenon | mg GRA/g DW | mg GBS/g DW | mg NGB/g DW | feruloyl-GLS/g DW | Total GLS |
|---|---|---|---|---|---|
| Control | 1.74 ± 0.06 | 2.08 ± 0.09 | 1.12 ± 0.09 | — | 4.94 ± 0.10 |
| Triton X-100 | 1.75 ± 0.06 | 2.16 ± 0.14 | 1.19 ± 0.15 | — | 5.10 ± 0.12 |

| Parthenon | mg GRA/g DW | mg GBS/g DW | mg NGB/g DW | feruloyl-GLS/g DW | Total GLS |
|---|---|---|---|---|---|
| INFLORESCENCE (mg/g DW) | | | | | |
| MPP | 1.73 ± 0.04 | 2.08 ± 0.12 | 1.08 ± 0.12 | — | 4.98 ± 0.15 |
| MeJA | 1.70 ± 0.10 | 2.05 ± 0.10 | 1.22 ± 0.12 | — | 4.97 ± 0.25 |
| MeJA + Triton X-100 | 2.09 ± 0.14 | 2.31 ± 0.15 | 2.75 ± 0.19 | — | 7.15 ± 0.33 |
| MeJA + MPP | 2.08 ± 0.16 | 2.76 ± 0.28 | 4.83 ± 0.26 | 1.08 ± 0.10 | 10.75 ± 0.38 |

GR: Glucoraphanin
GB: Glucobrassicin
MGB: Methoxyglucobrassicin
NGB: Neoglucobrassicin
F-GLS: feruloyl-GLS
Tr: concentration in trace amounts
DW. Dry weight As can be observed in Table 3, the application of Composition 1 (MeJA+MPP) achieves increases in the concentration of glucosinolates that are substantially higher than the rest of treatments applied to inflorescences and leaves and, moreover, it is the only one that achieves the appearance of a feruloyl-GLS. Composition 2 (MeJA+Triton X-100) which also favours the increase of glucosinolates but not the increase of a feruloyl-GLS, however, achieves a much lower increase (specifically 116% with composition 1, and 44% with composition 2).

Table 4.—Results of the percentage of commercial inflorescences of the Parthenon cultivarcultivar in the greenhouse test

| Parthenon | % of Commercial heads |
|---|---|
| Control | 100 |
| Triton X-100 | 81.1 |
| MPP | 100 |
| MeJA | 100 |
| MeJA + Triton X-100 | 58.4 |
| MeJA + MPP | 100 |

As can be observed in Table 4, the application of Composition 1 (MeJA+MPP) does not degrade the inflorescences, considering degradation as an irregular shape or colour alteration, which does ostensibly occur when another surfactant is used.

Drop Dispersion

Figure 3:
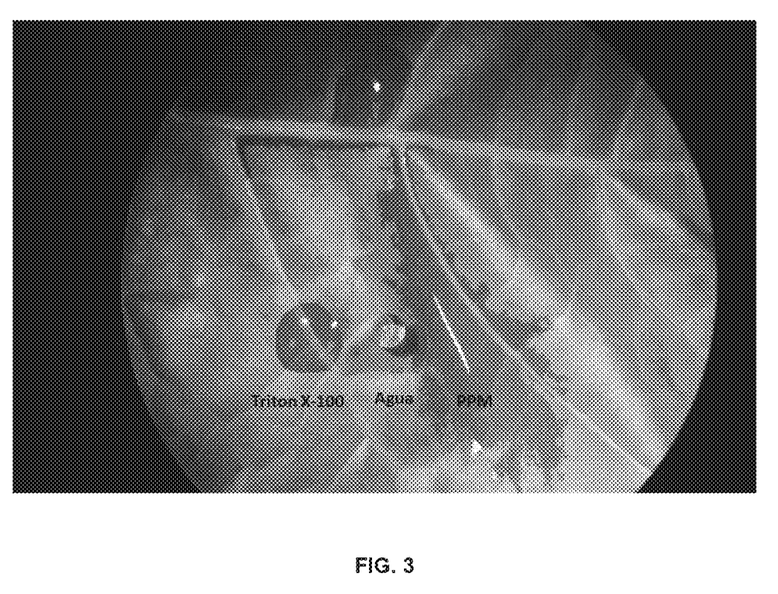
FIG. 3 shows the photograph showing the dispersion of a drop when methyl jasmonate is added with water, Triton X-100 and MPP (modified polysiloxane polyether).

The drop dispersion of Compositions 1 and 2 and that of elicitor Composition (MeJA) was determined under binoculars (1.6×) (FIG. 3). It can be seen that no dispersion is observed in the drop of MeJA, and that there is more dispersion in the drop of MeJA containing the Triton X-100 surfactant and total dispersion in the drop containing the MPP surfactant.

The calculated dispersion area of the drop indicates that Triton X-100 disperses 4 times more than water and MPP disperses 41 times more than water and 10 times more than Triton X-100 (see FIG. 3).

The invention claimed is:

1. A composition comprising methyl jasmonate (MeJA), a polysiloxane polyether, water and a C2-C4 alcohol, wherein:
   methyl jasmonate represents between 0.0015% and 0.0028% of the total volume thereof;
   polysiloxane polyether represents between 0.068% and 0.1272% of the total volume thereof;
   C2-C4 alcohol represents between 0.15% and 0.28% of the total volume thereof; and
   water represents the rest of the volume of the composition.

2. The composition according to claim 1, consisting of methyl jasmonate (MeJA), a polysiloxane polyether, water and a C2-C4 alcohol.

3. The composition according to claim 1, characterised in that the C2-C4 alcohol is ethanol.

4. The composition according to claim 2, characterised in that the volume consists of 0.0022% by volume of MeJA, 0.2% by volume of ethanol, 0.1% by volume of polysiloxane polyether and the rest is water to a total volume of 100%.

5. The composition according to claim 1, wherein the polysiloxane polyether is a non-ionic trisiloxane.

6. The composition according to claim 1, wherein the concentration of methyl jasmonate is between 50 and 500 molar.

7. The composition according to claim 6, wherein the concentration of methyl jasmonate is 100 molar.

8. A method for increasing the content of glucosinolates in an adult plant of the genus Brassica comprising the following steps:
   a) carrying out a first foliar application of the composition defined in claim 1, at the time the leaf bud appears on the plant;
   b) carrying out a second foliar application of the composition defined in claim 1, five days after the first application;
   c) carrying out a third foliar application of the composition defined in claim 1, five days after the second application.

9. The method according to claim 8, wherein the glucosinolates are selected from the list comprising glucoraphanin, glucobrassicin, methoxyglucobrassicin, neoglucobrassicin and combinations thereof.

10. The method according to claim 8, wherein the plant of the genus Brassica is selected from broccoli, cauliflower, cabbage, rapini, Brussels sprouts, swede, turnip, kohlrabi, kale and rapeseed.

11. The method according to claim 10, wherein the plant is broccoli.

12. The method according to claim 8, wherein an amount between 100 and 150 ml of the composition is applied in each of the applications.

13. The method according to claim 8, wherein the foliar application of the composition is by spray.

14. The method according to claim 8, wherein:
   the composition comprises 0.0022% by volume of MeJA, 0.2% by volume of ethanol, 0.1% by volume of polysiloxane polyether and water to a total volume of 100%.

15. A method to improve the defense mechanisms against herbivores and pathogens in a plant of the order Brassicales, said method comprising the use of the composition according to claim 1.

16. A method to obtain a functional food, said method comprising the use of the composition according to claim 1.

* * * * *

UNITED STATES PATENT AND TRADEMARK OFFICE
CERTIFICATE OF CORRECTION

PATENT NO. : 11,696,537 B2
APPLICATION NO. : 17/257743
DATED : July 11, 2023
INVENTOR(S) : Micaela Carvajal Alcaraz et al.

It is certified that error appears in the above-identified patent and that said Letters Patent is hereby corrected as shown below:

In the Claims

Column 12, Claim 7, Line 24, wherein "molar", should be --µmolar--.

Column 12, Claim 8, Line 26, wherein "molar", should be --µmolar--.

Signed and Sealed this
Ninth Day of January, 2024

Katherine Kelly Vidal
*Director of the United States Patent and Trademark Office*